United States Patent [19]

Walle

[11] 4,351,848

[45] Sep. 28, 1982

[54] 1-((1-METHYLETHYL)AMINO)-3-(((4-ALKYLTHIO)1-NAPHTHALENYL)OXY)-2-PROPANOL

[75] Inventor: Thomas Walle, Charleston, S.C.

[73] Assignee: Drug Science Foundation, Charleston, S.C.

[21] Appl. No.: 887,371

[22] Filed: Mar. 16, 1978

[51] Int. Cl.$^3$ .................. A01N 33/02; C07C 93/06
[52] U.S. Cl. .................. 424/330; 260/501.18; 260/501.19; 424/316; 564/349
[58] Field of Search .................. 260/570.7, 501.18; 424/316, 330; 564/349

[56] References Cited

U.S. PATENT DOCUMENTS

| | | | |
|---|---|---|---|
| 3,542,874 | 11/1970 | Keizer et al. | 260/570.7 |
| 3,712,890 | 1/1973 | Lee | 260/570.7 X |
| 3,857,839 | 12/1974 | Lee | 260/570.7 X |
| 3,888,898 | 6/1975 | Koppe et al. | 260/570.7 X |
| 3,937,834 | 2/1976 | Hunger et al. | 424/273 |
| 4,018,824 | 4/1977 | Tsukamoto et al. | 260/570.7 |

*Primary Examiner*—Robert V. Hines
*Attorney, Agent, or Firm*—Kenway & Jenney

[57] ABSTRACT

Alkylthiopropranolol, compositions, and methods of use in the treatment of cardio-vascular disorders in mammals.

6 Claims, No Drawings

1-((1-METHYLETHYL)AMINO)-3-(((4-ALKYLTHIO)1-NAPHTHALENYL)OXY)-2-PROPANOL

The invention described herein was in the course of work under a grant or award from the Department of Health and Human Services.

BACKGROUND OF THE INVENTION

Compounds of β-adrenergic blocking activity are of use in the treatment of certain cardio-vascular diseases such as hypertension, cardiac arrhythmia and angina pectoris.

The compound 1-((1-methylethyl)amino)-3-(((1-naphthalenyl)oxy)-propanol is described as a β-adrenergic blocking agent in U.S. Pat. No. 3,337,628. This compound has been used successfully as an anti-arrhythmic agent and in the treatment of angina pectoris. The compound 1-((1-methylethyl)amino)-3-(((6-methoxy)-1-naphthalenyl)oxy)-2-propanol hydrochloride has been described in U.S. Pat. No. 4,018,824. Other related compounds are found in U.S. Pat. Nos. 3,432,545; 3,935,267 and 3,937,834.

The thio analogues of the alkyloxypropanol compound have not been described in the literature, and their activity as β-blocking agents have not been established.

SUMMARY OF THE INVENTION

The present invention is directed to 1-((1-methylethyl)amino)-3-(((4-alkylthio)-1-naphthalenyl)-oxy)-2-propanol and the pharmaceutically-acceptable salts thereof. Compounds falling within the scope of the present invention may be represented by the general formula

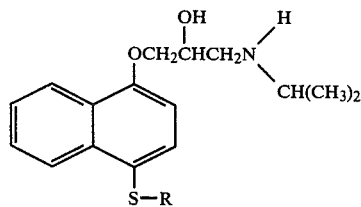

wherein R represents a lower alkyl having from one to about three carbon atoms. Compounds represented by the general formula given above have β-adrenergic blocking activity and are of use in the treatment of mammals suffering from cardiovascular disorders such as hypertension, cardiac arrhythmia and angina pectoris.

As noted above, the invention also includes the pharmaceutically-acceptable salts of the 1-((1-methylethyl)amino)-3-(((4-alkylthio)-1-naphthalenyl)oxy)-2-propanol compounds that are described herein. As used in the specification and claims, the term "pharmaceutically-acceptable salts" refers to non-toxic acid addition salts, the anions of which are relatively innocuous to animals at dosages consistent with good pharmacological activity so that the beneficial effects of the free base are not vitiated by the side effects ascribable to the anions. Pharmaceutically-acceptable salts include those derived from mineral acids such as hydrochloric and sulfuric acids and from organic acids such as lactic, maleic, succinic, fumaric, glutaric, citric, malic, p-toluenesulfonic, methanesulfonic and tartaric acids, and the like.

The present invention is also directed to a method for treating cardio-vascular disorders in a mammal which comprises, administering internally to said mammal a daily dosage of from about 0.2 to about 20 mg/kg per body weight of the compound 1-((1-methylethyl)amino)-3-(((4-alkylthio)-1-naphthalenyl)oxy)-2-propanol or a pharmaceutically-acceptable salt thereof. A third aspect of the present invention involves pharmaceutical compositions for the treatment of cardiovascular disorders in a mammal which comprise from about 10 to about 95 weight percent of an active alkylthiopropanol derivative described herein in combination with a pharmaceutically-acceptable carrier.

DETAILED DESCRIPTION OF THE INVENTION

Compounds within the scope of the present invention may be prepared from 4-(alkylthio)-1-naphthol which can be prepared according to the method of Ukai, et al., Chem. Phar. Bull 16, 606 (1968); Ibid 16, 195 (1968). Using procedures described in German patent 1,133,735 (which is hereby incorporated into this application by reference) the naphthol was treated with epichlorohydrin (3-chloro-1,2-epoxypropane) and a strong base ion exchange resin. The resulting intermediate is actually a mixture of the glycidyl ether of 4-(alkylthio)-1-naphthol and a small amount of the chlorohydrin. Separation of the reaction mixture is unnecessary, since both components react with isopropylamine to yield the desired 1-((1-methylethyl)amino)-3-(((4-alkylthio)-1-naphthalenyl)oxy)-2-propanol. This final step may be carried out in the absence of solvent, but the use of some solvent, as for example a lower alcohol, increases the rate of reaction.

If a water soluble derivative of the product is desired the compound may be readily converted to a pharmaceutically-acceptable salt by treatment with a preselected acid.

The preferred routes for administration of these compounds are by mouth and parenterally, however other routes may also be employed. For oral administration, the substances are usually prepared in pharmaceutical dosage forms such as tablets, capsules, elixirs, solutions or the like. In preparing dosage units intended for oral administration the active compound is usually mixed with a pharmaceutically-acceptable carrier, also referred to as an excipient. Commonly employed excipients include, for example, starch, gums, alcohols, sugars, fatty acids, etc. For parenteral administration, the compounds are administered in the form of an aqueous parenteral solution, generally admixed with conventional buffering agents, preservatives, etc.

The daily dosage range for compounds within the scope of this invention is from about 0.2 to about 20 mg/kg of body weight, with from about 1.0 to about 10 mg/kg being preferred. This daily dosage is preferrably administered in divided doses to be taken at timed intervals during the day. The exact dosage to be administered may vary depending upon the exact circumstances of administration such as for example the species of mammal, age of the mammal, the condition treated, the severity of the condition and the route of administration.

EXAMPLE 1

Preparation of 1-((methylethyl)-amino)-3-(((4-methylthio)-1-naphthalenyl)-oxy)-2-propanol (e.g. methylthiopropranolol)

A mixture containing 32.2 grams of 4-(alkylthio)-1-naphthol, 400 ml of epichlorohydrin, and 30 grams of DOWEX® 1-x10 resin (Dow Chemical Co.) was heated at reflux for 30 minutes. Thin layer chromatography indicated the presence of two products. The resin catalyst was removed by filtration, and the reaction mixture was washed with methylene chloride. The filtrate was concentrated to leave 63.1 grams of a light-colored liquid. A mixture of this material in 400 ml of ethanol and 400 ml of isopropylamine was heated at reflux for an additional 48 hours. Thin layer chromatography indicated the absence of starting material and the presence of product. The reaction was concentrated, partitioned between ether-water, and the separated ether phase was extracted with 10% hydrochloric acid. The aqueous extract was basified with 50% sodium hydroxide and extracted with ether. The ether layer was dried and concentrated to about 50 grams of oil which upon trituration with hexane gave the title compound as a white solid. The product was recrystallized from hot hexane. The final product had a melting point of 90°–92° C.

Elemental analysis showed carbon 67.0%, hydrogen 7.37%, and nitrogen 4.59% as compared to calculated values of carbon 66.9%, hydrogen 7.59%, and nitrogen 4.59% for the title compound.

The hydrochloride salt was prepared by dissolving 20 grams of the title compound in 75 ml of ethyl acetate. This solution was diluted with 275 ml of ether. Etheral hydrogen chloride was added until oiling no longer occurred. The mixture was cooled, the supernatant decanted, and the residue covered with ether. The residue was rubbed to a solid, collected, washed with ether and air dried. The 1-((methylethyl)amino)-3-(((4-methylthio)-1-naphthalenyl)oxy)-2-propanol hydrochloride was found to have a melting point of about 142°–147° C.

Elemental analysis showed carbon 59.5%, hydrogen 7% and nitrogen 4.18% as compared to calculated values of carbon 59.7%, hydrogen 7.1% and nitrogen 4.1% for the hydrochloride salt of the title compound.

EXAMPLE 2

The lipophilicity of methylthiopropranolol was investigated by measuring its partition coefficient between n-octanol and pH 7.4 (0.16 M phosphate) buffer.

The partition coefficient of methylthiopropanolol was found to be far higher than that of other beta blocking drugs, including propranolol. The partition ratio of methylthiopropranolol was 44, for propranolol 15, and for 4-methoxy-propranolol 15. This high lipid solubility of methylthiopropranolol would be predicted to enhance the ability to interact with biological membranes, including penetration into the central nervous system, which appears to be an important mode of action of this class of drugs. This property could also effect its duration of action through a more avid binding and availability to its site of action.

EXAMPLE 3

The effectiveness of methylthiopropranolol hydrochloride as a beta-adrenergic receptor blocking agent was demonstrated in anesthetized dogs. Intravenous injection of methylthiopropranolol in doses of 0.01 to 1 mg/kg (in aqueous 0.9% sodium chloride) was found to significantly reduce the positive inotropic and chronotropic effects of intravenous isoproterenol, a beta-adrenergic agonist drug, in a dose-dependent fashion. For example, methylthiopropranolol, 0.1 mg/kg, given intravenously produced approximately a 10-fold shift to the right in the contractile force and heart rate dose-response curved to isoproterenol (which was injected in dosages of 0.5 to 3 $\mu$g in aqueous 0.9% sodium chloride). In addition, methylthiopropranolol reduced the blood pressure lowering (depressor) effect of isoproterenol in a dose-dependent fashion with 0.1 mg/kg of methylthiopropranolol producing a 3-fold shift to the right in depressor dose-response curve of isoproterenol. The onset of these effects of methylthiopropranolol were within five minutes after its intravenous injection.

Propranolol, 0.1 mg/kg, produced about a 10-fold shift to the right in the contractile force and heart rate dose-response curves to isoproterenol and a 300-fold shift to the right in the isoproterenol depressor dose-response curve, in tests under the same conditions as for methylthiopropranolol.

These data indicate that methylthiopropranolol possesses significant beta-adrenergic blocking activity at both cardiac and vascular beta-adrenergic receptors. Furthermore, based upon the above data methylthiopropranolol appears to be more cardioselective in its beta blocking properties than propranolol.

EXAMPLE 4

The effects of methylthiopropranolol on vascular beta receptors was examined by determining the ability of methylthiopropranolol, 0.1 mg/kg, to block the vasodilator response to isoproterenol. Methylthiopropranolol, 0.1 mg/kg (dissolved in 0.9% aqueous solution of sodium chloride) injected intravenously in the anesthetized dog produced a 2-fold shift to the right in the dose-response curve for intra-arterial isoproterenol (0.3 to 3 $\mu$g in 0.9% aqueous solution of sodium chloride) induced increase in femoral artery blood flow. Propranolol, 0.1 mg/kg, studied in the same manner produced a 100-fold shift to the right in the isoproterenol dose-response curve.

These data indicate that methylthiopropranolol is less potent than propranolol as a beta-adrenergic blocking agent on vascular beta receptors.

EXAMPLE 5

The direct vasodilator effects of methylthiopropranolol were examined in the constantly perfused dog hindleg preparation. Intra-arterial injection of methylthiopropranolol hydrochloride (10–1000 $\mu$g in aqueous 0.9% sodium chloride) produced dose-related decreases in the hindleg perfusion pressure, i.e. vasodilatration. For example, in two experiments where methylthiopropranolol hydrochloride was injected intra-arterially, a 10 $\mu$g injection lowered perfusion pressure 9 mmHg while a 1000 $\mu$g injection lowered perfusion pressure 77 mmHg. Propranolol hydrochloride, in equivalent doses, in the same experiment, was only about 50% as potent as methylthiopropranolol in its ability to lower hindleg perfusion pressure.

Similarly, the vasodilator effects of methylthiopropranolol were studied by determining the effects of intra-arterial injection of the drug on femoral artery blood flow in the anesthetized dog. In nine experiments, methylthiopropranolol (10-1000 μg) produced dose-related increases in blood flow and was about twice as potent as propranolol for this effect.

Both groups of data indicate that methylthiopropranolol has vasodilator activity. In addition, methylthiopropranolol appears to be about twice as potent as propranolol for this effect.

EXAMPLE 6

The central hypotensive action of methylthiopropranolol was investigated by determining the effect of methylthiopropranolol, injected directly into the cerebrospinal fluid, on arterial pressure in anesthetized dogs and cats. The injection of methylthiopropranolol hydrochloride both into the cisterna magna of dogs (0.5 mg/kg in aqueous 0.9% sodium chloride) and into the lateral brain ventricle of cats (250-500 μg) in aqueous 0.9% sodium chloride) produced a prolonged hypotensive response and bradycardia. These data suggest that methylthiopropanolol has a hypotensive effect that is mediated by an action of the drug within the central nervous system.

EXAMPLE 7

The antihypertensive effects of methylthiopropranolol and propranolol were examined in the spontaneously hypertensive rat. Trained spontaneously hypertensive rats were fasted from food but not water from 8:00 A.M. to 12:00 A.M. and control blood pressure taken. They were then dosed orally with test compounds suspended or dissolved in METHOCEL$^R$ 0.5% and returned to their home cages with food and water. Dosages used were 60 mg/kg methylthiopropranolol hydrochloride; and 60 mg/kg propranolol hydrochloride. On the following day the rats were fasted from food from 8:00 A.M. to 12:00 P.M. then dosed as before. After a period of time (120 to 140 minutes) pressures were again taken. Treatments were assigned randomly to rats on day one but each rat received a repeat of his initial treatment on day 2. The data were analyzed using Analysis of Covariance. The data were compared with those from controls give the METHOCEL$^R$ solution only. Methylthiopropranolol significantly lowered blood pressure, P=<0.01, as compared to controls. Propranolol also lowered blood pressure (0.10>P>0.05).

These data indicate that methylthiopropranolol exerts an antihypertensive effect in the spontaneously hypertensive rat after oral dosing.

EXAMPLE 8

Methylthiopropranolol was compared with propranolol in the conscious normotensive rhesus monkey. With chronic oral dosage of from 5 mg/kg to 40 mg/kg daily given in divided doses over a period of 11 days, both drugs showed a lowering effect upon the heart rate. No blood pressure effects of the drugs were observed in the normotensive monkey.

These studies indicate that methylthiopropranolol has a cardiac slowing and probably beta-adrenergic blocking effect in the conscious normotensive monkey.

EXAMPLE 9

1-((methylethyl)amino)-3-(((4-methylthio)-1-naphthalenyl)oxy)-2-propanol hydrochloride reverted a sustained, ouabain induced, ventricular tachycardia to a sinus rhythm in three dogs.

Ouabain was administered (30 μg/kg intravenously in aqueous 0.9% sodium chloride) followed at 10 minute intervals by additional 10 μg/kg doses until a sustained ventricular tachycardia developed (as verified by electrocardiogram and right atrial electrocardiogram in conjunction with vegal stimulation). Methylthiopropranolol hydrochloride and propranolol hydrochloride were administered in doses of 0.5, 1.0, 1.5 and 2.0 mg/kg intravenously in aqueous 0.9% sodium chloride. The lowest dose of methylthiopropranolol hydrochloride which reverted the arrhythmia was 1.5 mg/kg; however, 1.0 mg/kg slowed the ventricular tachycardia from 210 per minute to 180 per minute. Duration of the sinus rhythm was between 4 and 8 minutes. This compares with the results observed following a comparable dose of propranolol hydrochloride.

In one of the three dogs the total dose of methylthiopropranolol hydrochloride, 2.0 mg/kg, was administered in a period of one minute and the arrhythmia reverted to a sinus rhythm within 5 seconds following injection.

These data indicate methylthiopropranolol hydrochloride produces a rapidly occurring antiarryhythmic action that is similar to the action produced by propranolol hydrochloride.

I claim:

1. A compound of the formula:

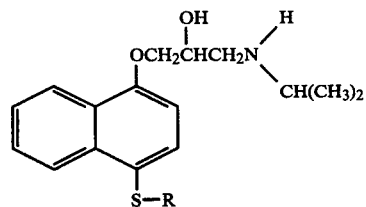

wherein R represents a lower alkyl having from 1 to about 3 carbon atoms; and the pharmaceutically-acceptable salts thereof.

2. The compound of claim 1 which is 1-((1-methylethyl)amino)-3-(((4-methylthio)-1-naphthalenyl)-oxy)-2-propanol; and the pharmaceutically-acceptable salts thereof.

3. A method for treating cardio-vascular disorders in a mammal which comprises administering internally to said mammal from about 0.2 to about 20 mg/kg of body weight per day of (1) a compound having the formula

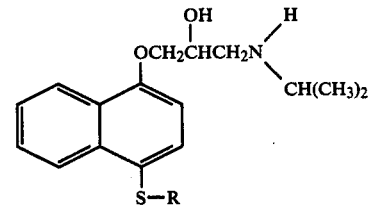

wherein R represents a lower alkyl having from 1 to about 3 carbon atoms or (2) a pharmaceutically-acceptable salt thereof.

4. The method of claim 3 wherein the compound is 1-((1-methylethyl)amino)-3-(((4-methyl-thio)-1-naphthalenyl)oxy)-2-propanol or a pharmaceutically-acceptable salt thereof.

5. A composition for the treatment of cardio-vascular disorders in a mammal which comprises a pharmaceutically-acceptable carrier in combination with a compound of the formula
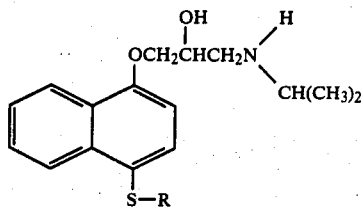
wherein R represents a lower alkyl having from 1 to about 3 carbon atoms; and the pharmaceutically-acceptable salts thereof.
6. The composition of claim 5 wherein the compound is 1-((1-methylethyl)amino)-3-(((4-methylthio)-1-naphthalenyl)oxy)-2-propanol or a pharmaceutically-acceptable salt thereof.
* * * * *